United States Patent [19]
Wagner et al.

[11] Patent Number: 5,951,991
[45] Date of Patent: Sep. 14, 1999

[54] CLEANSING PRODUCTS WITH IMPROVED MOISTURIZATION

[75] Inventors: Julie Ann Wagner; Erik John Hasenoehrl; Timothy John Fowler, all of Cincinnati, Ohio

[73] Assignee: The Procter & Gamble Company, Cincinnati, Ohio

[21] Appl. No.: 08/980,096

[22] Filed: Nov. 26, 1997

Related U.S. Application Data

[63] Continuation-in-part of application No. 08/861,748, May 22, 1997, abandoned.

[51] Int. Cl.$^6$ .............................. A61K 7/00; A61K 7/06; A01N 25/34
[52] U.S. Cl. .................. 424/401; 424/70.1; 424/402; 424/404; 442/43; 442/58
[58] Field of Search ................... 424/401, 402, 424/404, 70.1; 442/43, 58

[56] References Cited

U.S. PATENT DOCUMENTS

| | | |
|---|---|---|
| 2,877,115 | 3/1959 | Wemyss, Jr. et al. . |
| 2,944,931 | 7/1960 | Yang . |
| 3,305,392 | 2/1967 | Britt .......................................... 117/154 |
| 3,580,853 | 5/1971 | Parran ....................................... 252/152 |
| 3,632,396 | 1/1972 | Perez-Zamora ........................... 117/76 P |
| 3,686,025 | 8/1972 | Morton ................................ 117/140 R |
| 3,795,624 | 3/1974 | Feinstone .................................. 252/91 |
| 3,895,128 | 7/1975 | Gaiser ...................................... 428/43 |
| 3,896,807 | 7/1975 | Buchalter ................................. 128/261 |
| 3,944,694 | 3/1976 | McQueary ............................... 428/131 |
| 3,949,137 | 4/1976 | Akrongold et al. ...................... 428/311 |
| 3,956,551 | 5/1976 | Richards .................................. 428/88 |
| 4,145,302 | 3/1979 | Doan ........................................ 252/91 |
| 4,206,195 | 6/1980 | Bolich, Jr. et al. ........................ 424/16 |
| 4,206,196 | 6/1980 | Davis ........................................ 424/16 |
| 4,559,157 | 12/1985 | Smith et al. .............................. 252/90 |
| 4,574,052 | 3/1986 | Gupte et al. .............................. 252/90 |
| 4,690,821 | 9/1987 | Smith et al. .............................. 424/401 |
| 4,788,060 | 11/1988 | Endicott et al. ......................... 424/443 |
| 4,806,572 | 2/1989 | Kellett ...................................... 521/112 |
| 4,856,541 | 8/1989 | Kellett et al. ............................. 132/110 |
| 4,882,221 | 11/1989 | Bogart et al. ........................... 428/308.8 |
| 4,891,227 | 1/1990 | Thaman et al. .......................... 424/443 |
| 4,891,228 | 1/1990 | Thaman et al. .......................... 424/443 |
| 4,904,524 | 2/1990 | Yoh ....................................... 428/311.3 |
| 4,946,617 | 8/1990 | Sheridan et al. .......................... 252/91 |
| 4,948,585 | 8/1990 | Schlein .................................... 424/404 |
| 5,017,365 | 5/1991 | Niedbala .................................. 424/59 |
| 5,063,062 | 11/1991 | Greenspan et al. ...................... 424/443 |
| 5,538,732 | 7/1996 | Smith et al. .............................. 424/402 |
| 5,605,749 | 2/1997 | Pike et al. ................................. 442/60 |
| 5,661,170 | 8/1997 | Chodosh .................................. 514/390 |
| 5,683,971 | 11/1997 | Rose et al. ............................... 510/130 |
| 5,702,992 | 12/1997 | Martin et al. ............................ 442/123 |
| 5,763,332 | 6/1998 | Gordom et al. .......................... 442/84 |

FOREIGN PATENT DOCUMENTS

| | | |
|---|---|---|
| 1050066 | 3/1991 | China . |
| 1102211 | 5/1995 | China . |
| 1106704 | 8/1995 | China . |
| 1135320 | 11/1996 | China . |
| 186208 | 7/1986 | European Pat. Off. . |
| 0353013 | 1/1990 | European Pat. Off. . |
| 0 485 212 | 5/1992 | European Pat. Off. . |
| 0613675A1 | 9/1994 | European Pat. Off. . |
| 0615720A1 | 9/1994 | European Pat. Off. . |
| 63-097699 | 4/1988 | Japan . |
| 6-282290 | 6/1996 | Japan . |
| 9-151400 | 6/1997 | Japan . |
| 9-216809 | 8/1997 | Japan . |
| 1577926 | 10/1980 | United Kingdom . |
| 2163947 | 3/1986 | United Kingdom . |
| 2218430 | 11/1989 | United Kingdom . |
| 2297490 | 8/1996 | United Kingdom . |
| WO 89/03639 | 5/1989 | WIPO . |
| WO 93/21899 | 11/1993 | WIPO . |
| WO 94/27569 | 12/1994 | WIPO . |
| WO 95/00116 | 1/1995 | WIPO . |
| WO 95/16824 | 6/1995 | WIPO . |
| WO 95/31189 | 11/1995 | WIPO . |
| WO 96/06595 | 3/1996 | WIPO . |
| WO 96/14835 | 5/1996 | WIPO . |
| WO 96/24329 | 8/1996 | WIPO . |
| WO 96/24723 | 8/1996 | WIPO . |
| WO 96/34035 | 10/1996 | WIPO . |
| WO 96/36315 | 11/1996 | WIPO . |
| WO 97/07781 | 3/1997 | WIPO . |
| WO 97/16066 | 5/1997 | WIPO . |
| WO 97/45256 | 12/1997 | WIPO . |

OTHER PUBLICATIONS

Buf–Puf Singles Skin Conditioning, labeling, copyright 1991.
Buf–Puf Singles Oil–Free, labeling, copyright 1991.
Buf–Puf Singles With Cleanser for Normal to Dry Skin, labeling, copyright 1996.
Buf–Puf Singles With Cleanser for Normal to Oily Skin, labeling, copyright 1995.
Tender Bath, Westgate Laboratories, Edison, NJ, 1987. (Product Description—product believed to have been test marketed in Sep. 1986).

*Primary Examiner*—Shelley A. Dodson
*Assistant Examiner*—Marina Lamm
*Attorney, Agent, or Firm*—George W. Allen

[57] ABSTRACT

The present invention relates to a substantially dry, disposable, personal cleansing product useful for both cleansing and conditioning the skin or hair. These products are used by the consumer by wetting the dry product with water. The product comprises of a water insoluble substrate, a lathering surfactant, and a conditioning emulsion. The invention also encompasses methods for cleansing and conditioning the skin or hair using these products and to methods for manufacturing these products.

23 Claims, No Drawings

CLEANSING PRODUCTS WITH IMPROVED MOISTURIZATION

CROSS-REFERENCE TO RELATED APPLICATION

This application is a continuation-in-part of the now abandoned application entitled CLEANSING PRODUCTS WITH IMPROVED MOISTURIZATION and having U.S. Ser. No. 08/861,748, filed May 22, 1997 in the names of Julie Ann Wagner, Erik John Hasenoehrl and Timothy John Fowler.

TECHNICAL FIELD

The present invention relates to a substantially dry, disposable, personal cleansing product useful for both cleansing and conditioning the skin or hair. These products are used by the consumer by wetting the dry product with water. The product comprises a water insoluble substrate, a lathering surfactant, and a conditioning emulsion comprising (i) an external phase comprising an oil soluble agent and (ii) an internal phase comprising a water soluble conditioning agent. The product effectively delivers water soluble conditioning agents to the skin or hair.

Use of the substrate enhances lathering at low surfactant levels, increases cleansing and exfoliation, and optimizes delivery and deposition of water soluble conditioning ingredients. As a result, this invention provides effective cleansing using low levels of surfactant, and hence is less irritating, while providing superior conditioning benefits by delivering both water soluble conditioning agents and oil soluble conditioning agents.

The invention also encompasses products comprising various active ingredients for delivery to the skin or hair.

The invention also encompasses a method for cleansing and moisturizing the skin and hair using the products of the present invention and also to methods for manufacturing these products.

BACKGROUND OF THE INVENTION

Personal cleansing and conditioning products have traditionally been marketed in a variety of forms such as bar soaps, creams, lotions, and gels. These formulations have attempted to satisfy a number of criteria to be acceptable to consumers. These criteria include cleansing effectiveness, skin feel, mildness to skin, hair, and ocular mucosae, and lather volume. Ideal personal cleansers should gently cleanse the skin or hair, cause little or no irritation, and not leave the skin or hair overly dry after frequent use.

However, these traditional forms of personal cleansing products have the inherent problem of balancing cleansing efficacy against delivering a conditioning benefit. One solution to this problem is to use separate cleansing and conditioning products. However, this is not always convenient or practical and many consumers would prefer to use a single product which can both cleanse and condition the skin or hair. In a typical cleansing composition the conditioning ingredients are difficult to formulate because many conditioners are incompatible with the surfactants, resulting in an undesirable non-homogeneous mixture. To obtain a homogeneous mixture with conditioning ingredients, and to prevent the loss of conditioning ingredients before deposition, additional ingredients, e.g. emulsifiers, thickeners, and gellants are often added to suspend or emulsify the conditioning ingredients within the surfactant mixture. This results in an aesthetically pleasing homogeneous mixture, but often results in poor deposition of conditioning ingredients, because the conditioners are emulsified and not efficiently released during cleansing. Also, many conditioning agents have the disadvantage of suppressing lather generation. Lather suppression is a problem because many consumers seek cleansing products that provide a rich, creamy, and generous lather.

In addition, traditional formulations have been very ineffective in depositing water soluble conditioning agents to the skin or hair. It is desirable to deposit both oil soluble conditioning agents (e.g., emollients and lipids) and water soluble conditioning agents (e.g., humectants) to the skin in order to maximize acute and chronic skin conditioning benefits. With proper formulation techniques oil soluble agents can be deposited onto the skin or hair due to their inherent hydrophobic nature. However, deposition of water soluble conditioning agents with traditional cleansers is often difficult since water soluble conditioning agents typically rinse-away leaving only deposition of hydrophobic agents. Attempts have been made to deposit water soluble conditioning agents through the use of multiple emulsions (e.g., a water-in-oil-in-water emulsion). Although theoretically possible, this approach has been difficult in practice due to poor long-term shelf stability and product aesthetics.

The present invention eliminates this paradigm since the surfactants and the conditioning agents can be separately added directly onto the substrate. In this manner, the water soluble conditioning agents can simply be emulsified into an oil soluble agent and added to the substrate. This simple emulsion remains stable on the substrate and prevents the water soluble conditioning agent from being rinsed-away during the cleansing process since the water soluble conditioner is protected within the emulsion. As a result, the present invention effectively deposits both oil soluble and water soluble conditioning agents to the skin and hair.

Therefore, it is seen that conventional cleansing products which attempt to combine surfactants and both water soluble and oil soluble conditioning ingredients suffer from disadvantages inherently resulting from the incompatibilities of surfactants, water soluble conditioning agents, and oil soluble conditioning agents. A need clearly exists to develop cleansing systems which provide effective cleansing and yet deposit both water soluble and oil soluble conditioning agents in a single product.

It is also highly desirable to deliver cleansing and conditioning benefits from a disposable, single use product. Disposable products are convenient because they obviate the need to carry cumbersome bottles, bars, jars, tubes, and other forms of both cleansing and conditioning products. Disposable products are also a more sanitary alternative to the use of a sponge, washcloth, or other cleansing implement intended for multiple reuse, because such implements develop bacterial growth, unpleasant odors, and other undesirable characteristics related to repeated use.

It has been surprisingly found in the present invention that products can be developed to provide effective cleansing and conditioning in a convenient, cost effective, and sanitary disposable personal cleansing product. The present invention provides the convenience of not needing to use both a separate cleansing and conditioning product. The present invention is highly convenient to use because it is in the form of a substantially dry product that is wetted before use.

The present invention relates to a dry, disposable, personal cleansing product useful for both cleansing and conditioning the skin or hair. These products are used by the consumer by wetting the dry product with water. The product consists of a water insoluble substrate, a surfactant, and a conditioning emulsion. Without being limited by theory, it is believed that the substrate enhances lathering at low surfactant levels, increases cleansing and exfoliation, and optimizes delivery and deposition of both water soluble and oil soluble conditioning ingredients. As a result, this invention provides effective cleansing using low, and hence less irritating, levels of surfactant while providing superior conditioning benefits. It has also been found that these products are useful for delivering a wide range of active ingredients to the skin or hair during the cleansing process.

It is therefore, an object of the present invention to provide substantially dry products for both cleansing and conditioning the skin or hair wherein the products are used in combination with water.

It is another object of the present invention to provide products which deliver both water soluble conditioning agents and oil soluble conditioning agents to the skin or hair.

It is another object of the present invention to provide products which deliver water soluble conditioning agents to the skin or hair.

It is another object of the present invention to provide products comprising a water insoluble substrate, a surfactant, and a conditioning emulsion.

It is another object of the present invention to provide products which are disposable and intended for single use.

It is another object of the present invention to provide products which are mild to the skin or hair.

It is another object of the present invention to provide products useful for delivering active ingredients to the skin or hair during the cleansing and conditioning process.

It is another object of the present invention to provide methods of cleansing and conditioning the skin or hair.

It is another object of the present invention to provide methods of manufacturing the products of the present invention.

These and other objects of this invention will become apparent in light of the following disclosure.

SUMMARY OF THE INVENTION

The present invention relates to a disposable, single use personal care cleansing and conditioning product comprising:

(A) a water insoluble substrate,
(B) a lathering surfactant, and
(C) a conditioning emulsion,
wherein said product is substantially dry.

In further embodiments, the present invention relates to a disposable, single use personal care cleansing and conditioning product comprising:

(A) a water insoluble substrate,
(B) a lathering surfactant, and
(C) a conditioning emulsion comprising:
    (i) an internal phase comprising a water soluble conditioning agent, and
    (ii) an external phase comprising an oil soluble agent,
wherein said lathering surfactant and said conditioning emulsion are separately or simultaneously added onto or impregnated into said water insoluble substrate, and wherein said product is substantially dry.

In further embodiments, the present invention relates to a method of manufacturing a disposable, single use personal care cleansing and conditioning product comprising the step of separately or simultaneously adding onto or impregnating into a water insoluble substrate (A) a lathering surfactant, and
(B) a conditioning emulsion comprising,
    (i) an internal phase comprising a water soluble conditioning agent
    (ii) an external phase comprising an oil soluble agent, and
wherein said product is substantially dry.

In further embodiments, the present invention further comprises an emulsifier capable of forming an emulsion of said internal and external phase.

In further embodiments, the present invention relates to methods for cleansing and conditioning the skin or hair with the personal cleansing products described herein.

In even further embodiments, the present invention relates to methods of depositing conditioning agents to the skin or hair.

All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

DETAILED DESCRIPTION OF THE INVENTION

The personal cleansing products of the present invention are highly efficacious for cleansing the skin or hair, yet, provide effective deposition of water soluble conditioning agents. The present invention is also highly efficacious for cleansing and effectively depositing both water soluble and oil soluble conditioning agents. These products can also contain other active ingredients to be deposited onto the skin or hair.

Without being limited by theory it is believed that the substrate significantly contributes to generation of lather and deposition of conditioning agents and any other active ingredients. It is believed that this increase in lathering is the result of the surface action of the substrate. As a result, milder and significantly lower amounts of surfactants may be employed. The decreased amount of required surfactant is believed to relate to the decrease in the drying effect of the skin or hair by the surfactants. Furthermore, the decreased amount of surfactant dramatically lowers the inhibitory action (e.g., via emulsification or direct removal by the surfactants) of surfactants to deposition of conditioning agents.

Without being limited by theory, the substrate also enhances deposition of active ingredients and conditioning agents in addition to the conditioning agents in the conditioning emulsion. Since the invention is in dry form, the invention does not require additional emulsifiers to make the product homogeneous, which can inhibit deposition of conditioning agents and active ingredients. Furthermore, because the skin conditioners and active ingredients are dried onto or impregnated into the substrate, they are transferred directly to the skin or hair by surface contact of the wetted product to the skin.

Finally, the substrate also enhances cleansing. The substrate can have differing textures on each side, e.g. a rough side and a smooth side. The substrate acts as an efficient lathering and exfoliating implement. By physically coming into contact with the skin or hair, the substrate significantly aids in cleansing and removal of dirt, makeup, dead skin, and other debris.

By a "lathering surfactant" is meant a surfactant, which when combined with water and mechanically agitated generates a foam or lather. Preferably, these surfactants should be mild, which means that these surfactants provide sufficient cleansing or detersive benefits but do not overly dry the skin or hair, and yet meet the lathering criteria described above.

The terms "disposable" or "single use", are used herein in their ordinary sense to mean a product that is disposed or discarded after one usage event.

The term "water-activated," as used herein, means that the present invention is presented to the consumer in dry form to be used after wetting with water. It is found that these products produce a lather or are "activated" upon contact with water and further agitation.

The term "substantially dry" as used herein means that the product is substantially free of water and generally feels dry to the touch. The products of the present invention comprise less than about 15% by weight of water, preferably less than about 7.5% by weight of water, and more preferably less than about 3% by weight of water, the forgoing measured in a dry environment, e.g., low humidity. One of ordinary skill in the art would recognize that the water content of a product such as in the present invention can vary with the relative humidity of the environment.

The term "conditioning emulsion" as used herein means the combination of an internal phase comprising a water soluble conditioning agent that is enveloped by an external phase comprising an oil soluble agent. In preferred embodiments, the conditioning emulsion would further comprise an emulsifer.

The term "mild" as used herein in reference to the lathering surfactants and products of the present invention means that the products of the present invention demonstrate skin mildness comparable to a mild alkyl glyceryl ether sulfonate (AGS) surfactant based synthetic bar, i.e. synbar. Methods for measuring mildness, or inversely the irritancy, of surfactant containing products, are based on a skin barrier destruction test. In this test, the milder the surfactant, the lesser the skin barrier is destroyed. Skin barrier destruction is measured by the relative amount of radio-labeled (tritium labeled) water ($3H$—$H_2O$) which passes from the test solution through the skin epidermis into the physiological buffer contained in the diffusate chamber. This test is described by T. J. Franz in the *J. Invest. Dermatol.*, 1975, 64, pp. 190–195; and in U.S. Pat. No. 4,673,525, to Small et al., issued Jun. 16, 1987, which are both incorporated by reference herein in their entirety. Other testing methodologies for determining surfactant mildness well known to one skilled in the art can also be used.

The personal care products of the present invention comprise the following essential components: a water insoluble substrate; a lathering surfactant; and a conditioning emulsion. Additional active ingredients can also be included either on the substrate or within the emulsion. In addition, conditioning agents described in the conditioning emulsion section infra can be added onto the substrate separately from the conditioning emulsion. An alternative, preferred method is to apply the surfactant, the conditioning emulsion, and additional active ingredient separately to the substrate.

WATER INSOLUBLE SUBSTRATE

The products of the present invention comprise a water insoluble substrate. By "water insoluble" is meant that the substrate does not dissolve in or readily break apart upon immersion in water. The water insoluble substrate is the implement or vehicle for delivering the lathering surfactant and the conditioning component of the present invention to the skin or hair to be cleansed and conditioned. Without being limited by theory, it is believed that the substrate, by providing mechanical agitation provides a lather generating effect and also aids in the deposition of the conditioning component.

A wide variety of materials can be used as the substrate. The following nonlimiting characteristics are desirable: (i) sufficient wet strength for use, (ii) sufficient abrasivity, (iii) sufficient loft and porosity, (iv) sufficient thickness, and (v) appropriate size.

Nonlimiting examples of suitable insoluble substrates which meet the above criteria include nonwoven substrates, woven substrates, hydroentangled substrates, air entangled substrates, natural sponges, synthetic sponges, polymeric netted meshes, and the like. Preferred embodiments employ nonwoven substrates since they are economical and readily available in a variety of materials. By nonwoven is meant that the layer is comprised of fibers which are not woven into a fabric but rather are formed into a sheet, mat, or pad layer. The fibers can either be random (i.e., randomly aligned) or they can be carded (i.e. combed to be oriented in primarily one direction). Furthermore, the nonwoven substrate can be composed of a combination of layers of random and carded fibers.

Nonwoven substrates may be comprised of a variety of materials both natural and synthetic. By natural is meant that the materials are derived from plants, animals, insects or byproducts of plants, animals, and insects. By synthetic is meant that the materials are obtained primarily from various man-made materials or from natural materials which have been further altered. The conventional base starting material is usually a fibrous web comprising any of the common synthetic or natural textile-length fibers, or mixtures thereof.

Nonlimiting examples of natural materials useful in the present invention are silk fibers, keratin fibers and cellulosic fibers. Nonlimiting examples of keratin fibers include those selected from the group consisting of wool fibers, camel hair fibers, and the like. Nonlimiting examples of cellulosic fibers include those selected from the group consisting of wood pulp fibers, cotton fibers, hemp fibers, jute fibers, flax fibers, and mixtures thereof.

Nonlimiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers, polyurethane foam, and mixtures thereof. Examples of some of these synthetic materials include acrylics such as acrilan, creslan, and the acrylonitrile-based fiber, orlon; cellulose ester fibers such as cellulose acetate, arnel, and acele; polyamides such as nylons (e.g., nylon 6, nylon 66, nylon 610, and the like); polyesters such as fortrel, kodel, and the polyethylene terephthalate fiber, dacron; polyolefins such as polypropylene, polyethylene; polyvinyl acetate fibers; polyurethane foams and mixtures thereof. These and other suitable fibers and the nonwoven materials prepared therefrom are generally described in Riedel, "Nonwoven Bonding Methods and Materials," *Nonwoven World* (1987); *The Encyclopedia Americana*, vol. 11, pp. 147–153, and vol. 26, pp. 566–581 (1984); U.S. Pat. No. 4,891,227, to Thaman et al., issued Jan. 2, 1990; and U.S. Pat. No. 4,891,228 which are all incorporated by reference herein in their entirety.

Nonwoven substrates made from natural materials consist of webs or sheets most commonly formed on a fine wire screen from a liquid suspension of the fibers. See C. A. Hampel et al., *The Encyclopedia of Chemistry*, third edition, 1973, pp. 793–795 (1973); *The Encyclopedia Americana*, vol. 21, pp. 376–383 (1984); and G. A. Smook, *Handbook of Pulp and Paper Technologies*, Technical Association for the Pulp and Paper Industry (1986); which are incorporated by reference herein in their entirety.

Substrates made from natural materials useful in the present invention can be obtained from a wide variety of commercial sources. Nonlimiting examples of suitable commercially available paper layers useful herein include Airtex®, an embossed airlaid cellulosic layer having a base weight of about 71 gsy, available from James River, Green Bay, Wis.; and Walkisoft®, an embossed airlaid cellulosic having a base weight of about 75 gsy, available from Walkisoft U.S.A., Mount Holly, N.C.

Methods of making nonwoven substrates are well known in the art. Generally, these nonwoven substrates can be made by air-laying, water-laying, meltblowing, conforming, spunbonding, or carding processes in which the fibers or filaments are first cut to desired lengths from long strands, passed into a water or air stream, and then deposited onto a screen through which the fiber-laden air or water is passed. The resulting layer, regardless of its method of production or composition, is then subjected to at least one of several types of bonding operations to anchor the individual fibers together to form a self-sustaining web. In the present invention the nonwoven layer can be prepared by a variety of processes including hydroentanglement, thermally bonding or thermo-bonding, and combinations of these processes. Moreover, the substrates of the present invention can consist of a single layer or multiple layers. In addition, a multilayered substrate can include films and other nonfibrous materials.

Nonwoven substrates made from synthetic materials useful in the present invention can also be obtained from a wide variety of commercial sources. Nonlimiting examples of suitable nonwoven layer materials useful herein include HEF 40-047, an apertured hydroentangled material containing about 50% rayon and 50% polyester, and having a basis weight of about 43 grams per square yard (gsy), available from Veratec, Inc., Walpole, Mass.; HEF 140-102, an apertured hydroentangled material containing about 50% rayon and 50% polyester, and having a basis weight of about 56 gsy, available from Veratec, Inc., Walpole, Mass.; Novonet® 149-616, a thermo-bonded grid patterned material containing about 100% polypropylene, and having a basis weight of about 50 gsy, available from Veratec, Inc., Walpole, Mass.; Novonet® 149-801, a thermo-bonded grid patterned material containing about 69% rayon, about 25% polypropylene, and about 6% cotton, and having a basis weight of about 75 gsy, available from Veratec, Inc. Walpole, Mass.; Novonet® 149-191, a thermo-bonded grid patterned material containing about 69% rayon, about 25% polypropylene, and about 6% cotton, and having a basis weight of about 100 gsy, available from Veratec, Inc. Walpole, Mass.; HEF Nubtex® 149-801, a nubbed, apertured hydroentangled material, containing about 100% polyester, and having a basis weight of about 70 gsy, available from Veratec, Inc. Walpole, Mass.; Keybak® 951 V, a dry formed apertured material, containing about 75% rayon, about 25% acrylic fibers, and having a basis weight of about 43 gsy, available from Chicopee, New Brunswick, N.J.; Keybak® 1368, an apertured material, containing about 75% rayon, about 25% polyester, and having a basis weight of about 39 gsy, available from Chicopee, New Brunswick, N.J.; Duralace® 1236, an apertured, hydroentangled material, containing about 100% rayon, and having a basis weight from about 40 gsy to about 115 gsy, available from Chicopee, New Brunswick, N.J.; Duralace® 5904, an apertured, hydroentangled material, containing about 100% polyester, and having a basis weight from about 40 gsy to about 115 gsy, available from Chicopee, New Brunswick, N.J.; Sontaro 8868, a hydroentangled material, containing about 50% cellulose and about 50% polyester, and having a basis weight of about 60 gsy, available from Dupont Chemical Corp.

Alternatively, the water insoluble substrate can be a polymeric mesh sponge as described in European Patent No. EP 702550 A1 published Mar. 27, 1996, incorporated by reference herein in its entirety. The polymeric sponge comprises a plurality of plies of an extruded tubular netting mesh prepared from a strong flexible polymer, such as addition polymers of olefin monomers and polyamides of polycarboxylic acids. Although these polymeric sponges are designed to be used in conjunction with a liquid cleanser, these types of sponges can be used as the water insoluble substrate in the present invention.

The substrate can be made into a wide variety of shapes and forms including flat pads, thick pads, thin sheets, ball-shaped implements, irregularly shaped implements, and having sizes ranging from a surface area of about a square inch to about hundreds of square inches. The exact size will depend upon the desired use and product characteristics. Especially convenient are square, circular, rectangular, or oval pads having a surface area of from about 1 $in^2$ to about 144 $in^2$, preferably from about 10 $in^2$ to about 120 $in^2$, and more preferably from about 30 $in^2$ to about 80 $in^2$, and a thickness of from about 1 mil to about 500 mil, preferably from about 5 mil to about 250 mil, and more preferably from about 10 mil to about 100 mil.

The water insoluble substrates of the present invention can comprise two or more layers, each having different textures and abrasiveness. The differing textures can result from the use of different combinations of materials or from the use of different manufacturing processes or a combination thereof. A dual textured substrate can be made to provide the advantage of having a more abrasive side for exfoliation and a softer, absorbent side for gentle cleansing. In addition, separate layers of the substrate can be manufactured to have different colors, thereby helping the user to further distinguish the surfaces.

LATHERING SURFACTANT

The products of the present invention typically comprise from about 0.5% to about 40%, preferably from about 0.75% to about 20%, and more preferably from about 1% to about 10%, based on the weight of the water insoluble substrate, of a lathering surfactant.

By a lathering surfactant is meant a surfactant, which when combined with water and mechanically agitated generates a foam or lather. Preferably, these surfactants or combinations of surfactants should be mild, which means that these surfactants provide sufficient cleansing or detersive benefits but do not overly dry the skin or hair, and yet meet the lathering criteria described above.

A wide variety of lathering surfactants are useful herein and include those selected from the group consisting of anionic lathering surfactants, nonionic lather surfactants, amphotheric lathering surfactants, and mixtures thereof. Generally, the lathering surfactants do not strongly interfere with deposition of the conditioning agents, e.g., are fairly water soluble, and usually have an HLB value of above 10. Cationic surfactants can also be used as optional components, provided they do not negatively impact the overall lathering characteristics of the required, lathering surfactants.

Anionic Lathering Surfactants

Nonlimiting examples of anionic lathering surfactants useful in the compositions of the present invention are disclosed in McCutcheon's, *Detergents and Emulsifiers*, North American edition (1986), published by allured Publishing Corporation; McCutcheon's, *Functional Materials*, North American Edition (1992); and U.S. Pat. No. 3,929,678, to Laughlin et al., issued Dec. 30, 1975 all of which are incorporated by reference herein in their entirety.

A wide variety of anionic lathering surfactants are useful herein. Nonlimiting examples of anionic lathering surfactants include those selected from the group consisting of sarcosinates, sulfates, isethionates, taurates, phosphates, lactylates, glutamates and mixtures thereof. Amongst the isethionates, the alkoyl isethionates are preferred, and amongst the sulfates, the alkyl and alkyl ether sulfates are preferred. The alkoyl isethionates typically have the formula $RCO-OCH_2CH_2SO_3M$ wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, and mixtures thereof.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

$$R_1-SO_3-M$$

wherein $R_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Other anionic materials include phosphates such as monoalkyl, dialkyl, and trialkylphosphate salts.

Other anionic materials include alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and alkanolamine (e.g., triethanolamine), preferred examples of which are sodium lauroyl sarcosinate, sodium cocoyl sarcosinate, ammonium lauroyl sarcosinate, and sodium myristoyl sarcosinate. TEA salts of sarcosinates are also useful.

Also useful are taurates which are based on taurine, which is also known as 2-aminoethanesulfonic acid. Especially useful are taurates having carbon chains between $C_8$ and $C_{16}$. Examples of taurates include N-alkyltaurines such as the one prepared by reacting dodecylamine with sodium isethionate according to the teaching of U.S. Pat. No. 2,658,072 which is incorporated herein by reference in its entirety. Further nonlimiting examples include ammonium, sodium, potassium and alkanolamine (e.g., triethanolamine) salts of lauroyl methyl taurate, myristoyl methyl taurate, and cocoyl methyl taurate.

Also useful are lactylates, especially those having carbon chains between $C_8$ and $C_{16}$. Nonlimiting examples of lactylates include ammonium, sodium, potassium and alkanolamine (e.g., triethanolamine) salts of lauroyl lactylate, cocoyl lactylate, lauroyl lactylate, and caproyl lactylate.

Also useful herein as anionic surfactants are glutamates, especially those having carbon chains between $C_8$ and $C_{16}$. Nonlimiting examples of glutamates include ammonium, sodium, potassium and alkanolamine (e.g., triethanolamine) salts of lauroyl glutamate, myristoyl glutamate, and cocoyl glutamate.

Nonlimiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium lauroyl methyl taurate, sodium cocoyl methyl taurate, sodium lauroyl glutamate, sodium myristoyl glutamate, and sodium cocoyl glutamate and mixtures thereof.

Especially preferred for use herein is ammonium lauryl sulfate, ammonium laureth sulfate, sodium lauroyl lactylate, and triethanolamine lauroyl lactylate.

Nonionic Lathering Surfactants

Nonlimiting examples of nonionic lathering surfactants for use in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonionic lathering surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Alkyl glucosides and alkyl polyglucosides are useful herein, and can be broadly defined as condensation products of long chain alcohols, e.g. C8-30 alcohols, with sugars or starches or sugar or starch polymers, i.e., glycosides or polyglycosides. These compounds can be represented by the formula $(S)_n-O-R$ wherein S is a sugar moiety such as glucose, fructose, mannose, and galactose; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

Other examples of nonionic surfactants include amine oxides. Amine oxides correspond to the general formula $R_1R_2R_3NO$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

Nonlimiting examples of preferred nonionic surfactants for use herein are those selected form the group consisting of C8–C14 glucose amides, C8–C14 alkyl polyglucosides, sucrose cocoate, sucrose laurate, lauramine oxide, cocoamine oxide, and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc).

Preferred for use herein are amphoteric surfactants having the following structure:

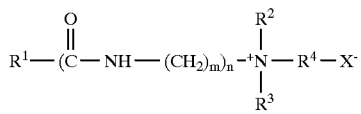

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected from the group consisting of $CO_2$, $SO_3$ and $SO_4$; $R^4$ is selected from the group consisting of saturated or unsaturated, straight or branched chain alkyl, unsubstituted or monosubstituted with hydroxy, having from 1 to about 5 carbon atoms. When X is $CO_2$, $R^4$ preferably has 1 or 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include the following compounds:

Cetyl dimethyl betaine (this material also has the CTFA designation cetyl betaine)

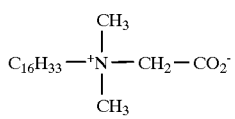

Cocamidopropylbetaine

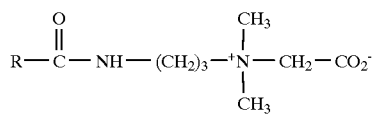

wherein R has from about 9 to about 13 carbon atoms
Cocamidopropyl hydroxy sultaine

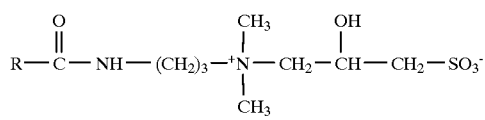

wherein R has from about 9 to about 13 carbon atoms,

Examples of other useful amphoteric surfactants are alkyliminoacetates, and iminodialkanoates and aminoalkanoates of the formulas $RN[CH_2)_mCO_2M]_2$ and $RNH(CH_2)_mCO_2M$ wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include amphoteric phosphates, such as coamidopropyl PG-dimonium chloride phosphate (commercially available as Monaquat PTC, from Mona Corp.). Also useful are amphoacetates such as disodium lauroamphodiacetate, sodium lauroamphoacetate, and mixtures thereof.

Preferred lathering surfactants for use herein are the following, wherein the anionic lathering surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium lauroyl lactylate, triethanolamine lauroyl lactylate, and mixtures thereof; wherein the nonionic lathering surfactant is selected from the group consisting of lauramine oxide, cocoamine oxide, decyl polyglucose, lauryl polyglucose, sucrose cocoate, C12–14 glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

CONDITIONING EMULSION

The products of the present invention comprise a conditioning emulsion which is useful for providing a conditioning benefit to the skin or hair during the use of the product. The conditioning emulsion comprises from about 0.25% to about 150%, preferably from about 0.5% to about 100%, and more preferably from about 1% to about 50% by weight of said water insoluble substrate. By a conditioning emulsion is meant a combination of an internal phase comprising a water soluble conditioning agent that is enveloped by an external phase comprising an oil soluble agent. In preferred embodiments, the conditioning emulsion would further comprise an emulsifer.

The conditioning emulsion of the present invention comprises (i) an internal phase comprising water soluble conditioning agents, and (ii) an external phase comprising oil soluble agents. In further embodiments, the conditioning emulsion further comprises an emulsifier capable of forming an emulsion of said internal and external phases. Although an emulsifier capable of forming an emulsion of the internal and external phases is preferred in the present invention, it is recognized in the art of skin care formulations that a water soluble conditioning agent can be enveloped by an oil soluble agent without an emulsifier. As long as the water soluble conditioning agent is enveloped by the oil soluble agent, thereby protected from being rinsed away during the cleansing process, the composition would be within the scope of the present invention.

The oil soluble agent is selected from one or more oil soluble agents such that the weighted arithmetic mean solubility parameter of the oil soluble agent is less than or equal to 10.5. The water soluble conditioning agent is selected from one or more water soluble conditioning agents such that the weighted arithmetic mean solubility parameter of the water soluble conditioning agent is greater than 10.5. It is recognized, based on this mathematical definition of solubility parameters, that it is possible, for example, to achieve the required weighted arithmetic mean solubility parameter, i.e. less than or equal to 10.5, for an oil soluble conditioning agent comprising two or more compounds if one of the compounds has an individual solubility parameter greater than 10.5. Conversely, it is possible to achieve the appropriate weighted arithmetic mean solubility parameter, i.e. greater than 10.5, for a water soluble conditioning agent comprising two or more compounds if one of the compounds has an individual solubility parameter less than or equal to 10.5.

Solubility parameters are well known to the formulation chemist of ordinary skill in the art and are routinely used as a guide for determining compatibilities and solubilities of materials in the formulation process.

The solubility parameter of a chemical compound, δ, is defined as the square root of the cohesive energy density for that compound. Typically, a solubility parameter for a compound is calculated from tabulated values of the additive group contributions for the heat of vaporization and molar volume of the components of that compound, using the following equation:

$$\delta = \left[\frac{\sum_i E_i}{\sum_i m_i}\right]^{1/2}$$

wherein $\Sigma_i E_i$=the sum of the heat of vaporization additive group contributions, and
$\Sigma_i m_i$=the sum of the molar volume additive group contributions
Standard tabulations of heat of vaporization and molar volume additive group contributions for a wide variety of atoms and groups of atoms are collected in Barton, A. F. M. *Handbook of Solubility Parameters*, CRC Press, Chapter 6, Table 3, pp. 64–66 (1985), which is incorporated by reference herein in its entirety. The above solubility parameter equation is described in Fedors, R. F., "A Method for Estimating Both the Solubility Parameters and Molar Volumes of Liquids", *Polymer Engineering and Science*, vol. 14, no. 2, pp. 147–154 (February 1974), which is incorporated by reference herein in its entirety.

Solubility parameters obey the law of mixtures such that the solubility parameter for a mixture of materials is given by the weighted arithmetic mean (i.e. the weighted average) of the solubility parameters for each component of that mixture. See, *Handbook of Chemistry and Physics*, 57th edition, CRC Press, p. C-726 (1976–1977), which is incorporated by reference herein in its entirety.

Formulation chemists typically report and use solubility parameters in units of $(cal/cm^3)^{1/2}$. The tabulated values of additive group contributions for heat of vaporization in the *Handbook of Solubility Parameters* are reported in units of kJ/mol. However, these tabulated heat of vaporization values are readily converted to cal/mol using the following well-known relationships:

1 J/mol=0.239006 cal/mol and 1000 J=1 kJ.

See Gordon, A. J. et al., *The Chemist's Companion*, John Wiley & Sons, pp. 456–463, (1972), which is incorporated by reference herein in its entirety.

Solubility parameters have also been tabulated for a wide variety of chemical materials. Tabulations of solubility parameters are found in the above-cited *Handbook of Solubility Parameters*. Also, see "Solubility Effects In Product, Package, Penetration, And Preservation", C. D. Vaughan, *Cosmetics and Toiletries*, vol. 103, October 1988, pp. 47–69, which is incorporated by reference herein in its entirety.

The External Phase of the Conditioning Emulsion

The external phase of the conditioning emulsion comprises an oil soluble agent. Any oil soluble agent or a combination of oil soluble agents having a weighted arithmetic mean solubility parameter of less than or equal to 10.5 can be used in the external phase. Preferably, the oil soluble agent is an oil soluble conditioning agent used to condition the skin or hair.

Nonlimiting examples of conditioning agents useful as oil soluble conditioning agents include those selected from the group consisting of mineral oil, petrolatum, C7–C40 branched chain hydrocarbons, C1–C30 alcohol esters of C1–C30 carboxylic acids, C1–C30 alcohol esters of C2–C30 dicarboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid monoesters and polyesters of sugars, polydialkylsiloxanes, polydiarylsiloxanes, polyalkarylsiloxanes, cylcomethicones having 3 to 9 silicon atoms, vegetable oils, hydrogenated vegetable oils, polypropylene glycol C4–C20 alkyl ethers, di C8–C30 alkyl ethers, and mixtures thereof.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p.415–417 (1993), which are incorporated by reference herein in their entirety.

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, *Drug. Cosmet. Ind.*, 89, 36–37, 76, 78–80, 82 (1961); and International Cosmetic Ingredient Dictionary, Fifth Edition, vol. 1, p. 537 (1993), which are incorporated by reference herein in their entirety.

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). Also useful are the C7–C40 isoparaffins, which are C7–C40 branched hydrocarbons.

Also useful are C1–C30 alcohol esters of C1–C30 carboxylic acids and of C2–C30 dicarboxylic acids, including straight and branched chain materials as well as aromatic derivatives. Also useful are esters such as monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, and propylene glycol diesters of C1–C30 carboxylic acids. Straight chain, branched chain and aryl carboxylic acids are included herein. Also useful are propoxylated and ethoxylated derivatives of these materials. Nonlimiting examples include diisopropyl sebacate, diisopropyl adipate, isopropyl myristate, isopropyl palmitate, myristyl propionate, ethylene glycol distearate, 2-ethylhexyl palmitate, isodecyl neopentanoate, di-2-ethylhexyl maleate, cetyl palmitate, myristyl myristate, stearyl stearate, cetyl stearate, behenyl behenate, dioctyl maleate, dioctyl sebacate, diisopropyl adipate, cetyl octanoate, diisopropyl dilinoleate, caprilic/capric triglyceride, PEG-6 caprylic/capric triglyceride, PEG-8 caprylic/capric triglyceride, and mixtures thereof.

Also useful are various C1–C30 monoesters and polyesters of glycerin and related materials. These esters are derived from glycerin and one or more carboxylic acid moities. Depending on the constituent acid and glycerin, these esters can be in either liquid or solid form at room temperature. Nonlimiting examples of solid esters include: glyceryl tribehenate, glyceryl stearate, glyceryl palmitate, glyceryl distearate, glyceryl dipalmitate.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. Other materials include cottonseed oil or soybean oil fatty acid esters of sucrose. The ester materials are further described in, U.S. Pat. No. 2,831, 854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517, 360, to Volpenhein, issued May 21, 1985; all of which are incorporated by reference herein in their entirety.

Nonvolatile silicones such as polydialkylsiloxanes, polydiarylsiloxanes, and polyalkarylsiloxanes are also useful oils. These silicones are disclosed in U.S. Pat. No. 5,069,897, to Orr, issued Dec. 3, 1991, which is incorporated by reference herein in its entirety. The polyalkylsiloxanes correspond to the general chemical formula $R_3SiO[R_2SiO]_xSiR_3$ wherein R is an alkyl group (preferably R is methyl or ethyl, more preferably methyl) and x is an integer up to about 500, chosen to achieve the desired molecular weight. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful herein include Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Also useful are materials such as trimethylsiloxysilicate, which is a polymeric material corresponding to the general chemical formula $[(CH_2)_3SiO_{1/2}]_x[SiO_2]y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer up to about 500, chosen to achieve the desired molecular weight. Commercially available dimethiconols are typically sold as mixtures with dimethicone or cyclomethicone (e.g. Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation).

Vegetable oils and hydrogenated vegetable oils are also useful herein. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are C4–C20 alkyl ethers of polypropylene glycols, C1–C20 carboxylic acid esters of polypropylene glycols, and di-C8–C30 alkyl ethers. Nonlimiting examples of these materials include PPG-14 butyl ether, PPG-15 stearyl ether, dioctyl ether, dodecyl octyl ether, and mixtures thereof.

Internal Phase of the Conditioning Emulsion

The internal phase of the conditioning emulsion comprises a water soluble conditioning agent. Any water soluble conditioning agent or a combination of water soluble conditioning agents having a weighted arithmetic mean solubility parameter of greater than 10.5 can be used in the internal phase. In addition, any water soluble ingredient listed in the "Additional Ingredients" and "Active Ingredients" may be incorporated into the internal phase of the conditioning emulsion provided that the water soluble ingredient is compatible with the water soluble conditioning agent and does not promote instability of the conditioning emulsion.

Nonlimiting examples of conditioning agents useful as water soluble conditioning agents include those selected from the group consisting of polyhydric alcohols, polypropylene glycols, polyethylene glycols, ureas, pyrolidone carboxylic acids, ethoxylated and/or propoxylated C3–C6 diols and triols, alpha-hydroxy C2–C6 carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful water soluble conditioning agents include materials such as urea; guanidine; glycolic acid and glycolate salts (e.g., ammonium and quaternary alkyl ammonium); lactic acid and lactate salts (e.g. ammonium and quaternary alkyl ammonium); sodium PCA; sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; panthenol; niacinamide; and mixtures thereof. Also useful are materials such as aloe vera in any of its variety of forms (e.g., aloe vera gel), chitin, honey extract, starch-grafted sodium polyacrylates such as Sanwet (RTM) IM-1000, IM-1500, and IM-2500 (available from Celanese Superabsorbent Materials, Portsmouth, Va.); lactamide monoethanolanine; acetamide monoethanolamine; and mixtures thereof. Also useful are propoxylated glycerols as described in propoxylated glycerols described in U.S. Pat. No. 4,976,953, to Orr et al., issued Dec. 11, 1990, which is incorporated by reference herein in its entirety.

The internal phase can also optionally comprise water. Just enough water to solubilize the water soluble conditioning agent is needed. In general, the amount of water varies depending upon the material that needs to be dissolved, e.g., solubility in water and rheology. Thus, water soluble agents, which are solid or very viscous at processing temperatures, require more water than a material which is less viscous or liquid at processing temperatures. Similarly, water soluble conditioning agents which have high solubility in water would require less water than conditioning agents that have low solubility in water.

The internal phase can optionally comprise other water-soluble or dispersible materials that do not adversely affect the stability of the conditioning emulsion. One such material is a water-soluble electrolyte. The dissolved electrolyte minimizes the tendency of materials present in the lipid phase to also dissolve in the water phase. Any electrolyte capable of imparting ionic strength to the internal phase can be used. Suitable electrolytes include the water soluble mono-, di- or trivalent inorganic salts such as water-soluble halides, e.g., chlorides, nitrates and sulfates of alkali metals and alkaline earth metals. Examples of such electrolytes include sodium chloride, calcium chloride, sodium sulfate, magnesium sulfate, and sodium bicarbonate. The electrolyte will typically be included in a concentration in the range of from about 1 to about 20% of the internal phase.

Other water-soluble or dispersible materials that can be present in the internal phase include thickeners and viscosity modifiers. Suitable thickeners and viscosity modifiers include water-soluble polyacrylic and hydrophobically modified polyacrylic resins such as Carbopol and Pemulen, starches such as corn starch, potato starch, tapioca, gums such as guar gum, gum arabic, cellulose ethers such as hydroxypropyl cellulose, hydroxyethyl cellulose, carboxymethyl cellulose, and the like. These thickeners and viscosity modifiers will typically be included in a concentration in the range of from about 0.05 to about 0.5% of the internal phase.

Other water soluble or dispersible materials that can be present in the internal water phase include polycationic polymers to provide steric stabilization at the water-lipid interface and nonionic polymers that also stabilize the water-in-lipid-emulsion. Suitable polycationic polymers include Reten 201, Kymene 557H® and Acco 7112. Suitable nonionic polymers include polyethylene glycols (PEG) such as Carbowax. These polycationic and nonionic polymers will typically be included in a concentration in the range of from about 0.1 to about 1.0% of the internal phase.

The Emulsifier

Preferred embodiments of the present invention which contain conditioning emulsions comprise an emulsifier capable of forming an emulsion of the internal and external phases. In the emulsions of the present invention, the emulsifier is included in an effective amount. What constitutes an "effective amount" will depend on a number of factors including the respective amounts of the oil soluble agents, the type of emulsifier used, the level of impurities present in the emulsifier, and like factors. Typically, the emulsifier comprises from about 0.1% to about 20%, preferably from about 1% to about 10%, and more preferably from about 3% to about 6% by weight of the conditioning emulsion.

The emulsifiers useful in the present invention typically are oil soluble or miscible with the oil soluble external phase materials, especially at the temperature at which the lipid material melts. It also should have a relatively low HLB value. Emulsifiers suitable for use in the present invention have HLB values typically in the range of from about 1 to about 10 and can include mixtures of different emulsifiers. Preferably, these emulsifiers will have HLB values from about 1.5 to about 9.5, and more preferably from about 2 to about 9. Emulsifiers having HLB values of from about 1 to about 7, more preferably from about 1.5 to about 6 and most preferably from about 2 to about 5 are also suitable.

A wide variety of emulsifiers are useful herein and include, but not limited to, those selected from the group consisting of sorbitan esters, glyceryl esters, polyglyceryl esters, methyl glucose esters, sucrose esters, ethoxylated fatty alcohols, hydrogenated castor oil ethoxylates, sorbitan ester ethoxylates, polymeric emulsifiers, and silicone emulsifiers.

Sorbitan esters are useful in the present invention. Preferable are sorbitan esters of C16–C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan laurate, sorbitan palmitate, sorbitan monooleate (e.g., SPAN® 80), sorbitan sesquioleate (e.g., Arlacel® 83), sorbitan monoisostearate (e.g., CRILL® 6 made by Croda), sorbitan stearates (e.g., SPAN® 60), sorbitan triooleate (e.g., SPAN® 85), sorbitan tristearate (e.g., SPAN® 65), sorbitan dipalmitates (e.g., SPAN® 40), and sorbitan isostearate. Sorbitan laurate, sorbitan monoisostearate and sorbitan palmitate are particularly preferred emulsifiers for use in the present invention.

Other suitable emulsifiers for use in the present invention include, but is not limited to, glyceryl monoesters, preferably glyceryl monoesters of C16–C22 saturated, unsaturated and branched chain fatty acids such as glyceryl oleate, glyceryl monostearate, glyceryl monopalmitate, glyceryl monobehenate, and mixtures thereof, polyglyceryl esters of C16–C22 saturated, unsaturated and branched chain fatty acids, such as polyglyceryl-2 isostearate, polyglyceryl-4 stearate, polyglyceryl-4 isostearate, polyglyceryl-4 tristearate, polyglyceryl-4 pentastearate, polyglyceryl-3 oleate, diglycerol monooleate, diglyceryl monostearate, tetraglycerol monooleate, decaglyceryl stearate, decaglyceryl dipalmitate, decaglyceryl distearate, decaglyceryl decastearate decaglyceryl pentastearate and mixtures thereof; methyl glucose esters, preferably methyl glucose esters of C16–C22 saturated, unsaturated and branched chain fatty acids such as methyl glucose dioleate, methyl glucose sesquiisostearate, and mixtures thereof; sucrose fatty acid esters, preferably sucrose esters of C12–C22 saturated, unsaturated and branched chain fatty acids such as sucrose stearate, sucrose trilaurate, sucrose distearate (e.g., Crodesta® F10), and mixtures thereof; C12–C22 ethoxylated fatty alcohols such as oleth-2, oleth-3, steareth-2, and mixtures thereof; hydrogenated castor oil ethoxylates such as PEG-7 hydrogenated castor oil; sorbitan ester ethoxylates such as PEG-40 sorbitan peroleate, Polysorbate-80, and mixtures thereof; polymeric emulsifiers such as ethoxylated dodecyl glycol copolymer; and silicone emulsifiers such as laurylmethicone copolyol, cetyldimethicone, dimethicone copolyol, and mixtures thereof.

In addition to these primary emulsifiers, the compositions of the present invention can optionally contain a coemulsifier to provide additional water-lipid emulsion stability. Suitable coemulsifiers include, but is not limited to, phosphatidyl cholines and phosphatidyl choline-containing compositions such as lecithins; long chain C16–C22 fatty acid salts such as sodium stearate; long chain C16–C22 dialiphatic, short chain Cl-C4 dialiphatic quaternary ammonium salts such as ditallow dimethyl ammonium chloride and ditallow dimethyl ammonium methylsulfate; long chain C16–C22 dialkoyl(alkenoyl)-2-hydroxyethyl, short chain C1–C4 dialiphatic quaternary ammonium salts such as ditallowoyl-2-hydroxyethyl dimethyl ammonium chloride; the long chain C16–C22 dialiphatic imidazolinium quaternary ammonium salts such as methyl-1-tallow amido ethyl-2-tallow imidazolinium methylsulfate and methyl-1-oleyl amido ethyl-2-oleyl imidazolinium methylsulfate; short chain C1–C4 dialiphatic, long chain C16–C22 monoaliphatic benzyl quaternary ammonium salts such as dimethyl stearyl benzyl ammonium chloride, and synthetic phospholipids such as stearamidopropyl PG-dimonium chloride (Phospholipid PTS from Mona Industries).

ADDITIONAL INGREDIENTS

The products of the present invention can comprise a wide range of optional ingredients. Some of these ingredients are listed in more detail herein. Particularly useful are various active ingredients useful for delivering various benefits of the skin or hair during the cleansing and conditioning process. If the ingredient is compatible with the internal or external phases of the conditioning emulsion, the ingredient can be incorporated into the appropriate phases. This is especially true with water soluble active ingredients which are compatible with the internal phase and do not promote instability of the conditioning emulsion. In these compositions, the product is useful for delivering the active ingredient to the skin or hair.

Furthermore, any of the conditioning agents described above in sections describing the internal (water soluble) and external (oil soluble) phases of the conditioning emulsion may be added to the substrate separately from the conditioning emulsion.

ACTIVE INGREDIENTS

The compositions of the present invention can comprise a safe and effective amount of one or more active ingredients or pharmaceutically-acceptable salts thereof.

The term "safe and effective amount" as used herein, means an amount of an active ingredient high enough to modify the condition to be treated or to deliver the desired skin benefit, but low enough to avoid serious side effects, at a reasonable benefit to risk ratio within the scope of sound medical judgment. What is a safe and effective amount of the active ingredient will vary with the specific active, the ability of the active to penetrate through the skin, the age, health condition, and skin condition of the user, and other like factors.

The active ingredients useful herein can be categorized by their therapeutic benefit or their postulated mode of action. However, it is to be understood that the active ingredients useful herein can in some instances provide more than one therapeutic benefit or operate via more than one mode of action. Therefore, classifications herein are made for the sake of convenience and are not intended to limit the active ingredient to that particular application or applications listed. Also, pharmaceutically-acceptable salts of these active ingredients are useful herein. The following active ingredients are useful in the compositions of the present invention.

Anti-Acne Actives:

Examples of useful anti-acne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives:

Examples of antiwrinkle and anti-skin atrophy actives include retinoic acid and its derivatives (e.g., cis and trans); retinol; retinyl esters; salicylic acid and derivatives thereof; sulfur-containing D and L amino acids and their derivatives and salts, particularly the N-acetyl derivatives, a preferred example of which is N-acetyl-L-cysteine; thiols, e.g. ethane thiol; hydroxy acids, phytic acid, lipoic acid; lysophosphatidic acid, and skin peel agents (e.g., phenol and the like); ascorbic acid and its derivatives.

Non-Steroidal Anti-Inflammatory Actives (NSAIDS):

Examples of NSAIDS include the following categories: propionic acid derivatives; acetic acid derivatives; fenamic acid derivatives; biphenylcarboxylic acid derivatives; and oxicams. All of these NSAIDS are fully described in U.S. Pat. No. 4,985,459 to Sunshine et al., issued Jan. 15, 1991, incorporated by reference herein in its entirety. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics:

Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Artificial Tanning Agents and Accelerators:

Examples of artificial tanning agents and accelerators include dihydroxyacetone, tyrosine, tyrosine esters such as ethyl tyrosinate, and phospho-DOPA.

Antimicrobial and Antifungal Actives:

Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione and clotrimazole.

Preferred examples of actives useful herein include those selected from the group consisting of salicylic acid, benzoyl peroxide, 3-hydroxy benzoic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, ascorbic acid and derivatives thereof, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, neocycin sulfate, and mixtures thereof.

Sunscreen Actives:

Also useful herein are sunscreening actives. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*, all of which are incorporated herein by reference in their entirety. Nonlimiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat. No. 4,999,186, to Sabatelli et al., issued Mar. 12, 1991; these two references are incorporated by reference herein in their entirety. Especially preferred examples of these sunscreens include those selected from the group consisting of 4-N,N-(2-ethylhexyl)methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethoxy) dibenzoylmethane, and mixtures thereof. Exact amounts of sunscreens which can be employed will vary depending upon the sunscreen chosen and the desired Sun Protection Factor (SPF) to be achieved. SPF is a commonly used measure of photoprotection of a sunscreen against erythema. See *Federal Register*, Vol. 43, No. 166, pp. 38206–38269, Aug. 25, 1978, which is incorporated herein by reference in its entirety.

Nonlimiting examples of preferred actives useful herein include those selected from the group consisting of salicylic acid, benzoyl peroxide, cis-retinoic acid, trans-retinoic acid, retinol, retinyl palmitate, ascorbic acid, phytic acid, N-acetyl L-cysteine, azelaic acid, lipoic acid, resorcinol, ibuprofen, naproxen, hydrocortisone, phenoxyethanol, phenoxypropanol, phenoxyisopropanol, 2,4,4,'-trichloro-2'-hydroxy diphenyl ether, 3,4,4'-trichlorocarbanilide, 2-ethylhexyl p-methoxycinnamate, oxybenzone, 2-phenylbenzimidozole-5-sulfonic acid, dihydroxyacetone, and mixtures thereof.

Cationic Surfactants

The products of the present invention can also optionally comprise one or more cationic surfactants, provided these materials are selected so as not to interfere with the overall lathering characteristics of the required, lathering surfactants.

Nonlimiting examples of cationic surfactants useful herein are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonlimiting examples of cationic surfactants useful herein include cationic alkyl ammonium salts such as those having the formula:

$$R_1R_2R_3R_4N^+X^-$$

wherein $R_1$, is selected from an alkyl group having from about 12 to about 18 carbon atoms, or aromatic, aryl or alkaryl groups having from about 12 to about 18 carbon atoms; $R_2$, $R_3$, and $R_4$ are independently selected from hydrogen, an alkyl group having from about 1 to about 18 carbon atoms, or aromatic, aryl or alkaryl groups having from about 12 to about 18 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain ether linkages, or hydroxy or amino group substituents (e.g., the alkyl groups can contain polyethylene glycol and polypropylene glycol moieties).

More preferably, $R_1$ is an alkyl group having from about 12 to about 18 carbon atoms; $R_2$ is selected from H or an alkyl group having from about 1 to about 18 carbon atoms; $R_3$ and $R_4$ are independently selected from H or an alkyl group having from about 1 to about 3 carbon atoms; and X is as described in the previous paragraph.

Most preferably, $R_1$ is an alkyl group having from about 12 to about 18 carbon atoms; $R_2$, $R_3$, and $R_4$ are selected from H or an alkyl group having from about 1 to about 3 carbon atoms; and X is as described previously.

Alternatively, other useful cationic surfactants include amino-amides, wherein in the above structure $R_1$ is alternatively $R_5CO-(CH_2)_n-$, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, dicetyl ammonium chloride, dicetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof. Additional quaternary ammonium salts include those wherein the C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium salts derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Preferred cationic surfactants useful herein include those selected from the group consisting of dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, and mixtures thereof.

Other Optional Ingredients

The compositions of the present invention can comprise a wide range of other optional components. These additional components should be pharmaceutically acceptable. The *CTFA Cosmetic Ingredient Handbook*, Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these and other functional classes include: abrasives, absorbents, anticaking agents, antioxidants, vitamins, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, preservatives, propellants, reducing agents, skin bleaching agents, and sunscreening agents.

Also useful herein are aesthetic components such as fragrances, pigments, colorings, essential oils, skin sensates, astringents, skin soothing agents, and skin healing agents.

METHODS OF MANUFACTURE

The disposable, single use personal care cleansing and conditioning products of the present invention are manufactured by separately or simultaneously adding onto or impregnating into a water insoluble substrate a lathering surfactant and a conditioning emulsion, wherein said resulting product is substantially dry. By "separately" is meant that the surfactants and conditioning agents can be added sequentially, in any order without first being combined together. By "simultaneously" is meant that the surfactants and conditioning agents can be added at the same time, with or without first being combined together.

For example, the lathering surfactants can first be added onto or impregnated into the water insoluble substrate followed by the conditioning emulsions, or vice versa. Alternatively, the lathering surfactants and conditioning emulsions can be added onto or impregnated into the water insoluble substrate at the same time.

The surfactant, conditioning emulsions, and any optional ingredients can be added onto or impregnated into the water insoluble substrate by any means known to those skilled in the art: for example, by spraying, printing, splashing, dipping, soaking, or coating. The optional ingredients may be the same as those in the internal or external phases of the conditioning emulsion.

In preparing the articles according to the present invention, the conditioning emulsion is initially formulated. Typically, this is achieved by blending or melting together the oil soluble, external phase components and the emulsifier. The particular temperature to which this oil soluble agent/emulsifier mixture is heated will depend on the melting point of the oil soluble external phase components. Typically, this oil soluble agent/emulsifier is heated to a temperature in the range from about 60° C. to about 90° C., preferably from about 70° C. to about 80° C., prior to being mixed, blended or otherwise combined with the water soluble internal phase components. However, heating is not always required to form the conditioning emulsion. The melted oil soluble agent/emulsifier mixture is then blended with the water phase components and then mixed together to provide the emulsion.

When water or moisture is used or present in the manufacturing process, the resulting treated substrate is then dried so that it is substantially free of water. The treated substrate can be dried by any means known to those skilled in the art. Nonlimiting examples of known drying means include the use of convection ovens, radiant heat sources, microwave ovens, forced air ovens, and heated rollers or cans. Drying also includes air drying without the addition of heat energy, other than that present in the ambient environment. Also, a combination of various drying methods can be used.

METHODS OF CLEANSING AND CONDITIONING THE SKIN OR HAIR

The present invention also relates to a method of cleansing and conditioning the skin or hair with a personal cleansing product of the present invention. These methods comprise the steps of wetting with water a substantially dry, disposable, single use personal cleansing product comprising a water insoluble substrate, a lathering surfactant, and a conditioning component, and contacting the skin or hair with said wetted product. In further embodiments, the present invention is also useful for delivering various active ingredients to the skin or hair.

The products of the present invention are substantially dry and are intended to be wetted with water prior to use. The product is wetted by immersion in water or by placing it under a stream of water. Lather is generated from the product by mechanically agitating and/or deforming the product either prior to or during contact of the product with the skin or hair. The resulting lather is useful for cleansing and conditioning the skin or hair. During the cleansing process and subsequent rinsing with water, the conditioning agents and active ingredients are deposited onto the skin or hair. Deposition of conditioning agents and active ingredients are enhanced by the physical contact of the substrate with the skin or hair.

DEPOSITION OF THE CONDITIONING COMPONENT ONTO THE SKIN OR HAIR

The compositions of the present invention are useful for depositing the conditioning components of the present invention to the skin or hair. In further embodiments where an active ingredient is present, the compositions are also useful for depositing the active ingredient to the skin or hair.

The compositions of the present invention preferably deposit greater than about 2.5 micrograms/cm$^2$, more preferably greater than about 5 micrograms/cm$^2$, more preferably greater than about 10 micrograms/cm$^2$, and most preferably greater than about 25 micrograms/cm$^2$ of the conditioning component to the skin or hair during use of the product.

The present invention also relates to a method of depositing greater than about 2.5 micrograms/cm$^2$, preferably greater than about 5 micrograms/cm$^2$, more preferably greater than bout 10 micrograms/cm$^2$, and most preferably greater than about 25 micrograms/cm$^2$ of the conditioning agent to the surface of the skin or hair.

Quantitation of the conditioning component deposited on the skin or hair can be measured using a variety of standard analytical techniques well known to the chemist of ordinary skill in the art. Such methods include for instance extraction of an area of the skin or hair with a suitable solvent followed by analysis by chromatography (i.e. gas chromatography, liquid chromatography, supercritical fluid chromatography, etc.), IR spectroscopy, UV/VIS spectroscopy, mass spectrometry, etc. Direct measurements can also be made on the skin or hair by techniques such as IR spectroscopy, UV/VIS spectroscopy, opacity measurements, fluoresce spectroscopy, ESCA spectroscopy, and the like.

In a typical method for measuring deposition, a product of the present invention is wetted with water and squeezed and agitated to generate a lather. The product is then rubbed for approximately 15 seconds on a site, approximately about 25 cm$^2$ to about 300 cm$^2$, preferably about 50 cm$^2$ to about 100 cm$^2$, on the skin or head which has been demarcated using an appropriate indelible marker. The site is then rinsed for approximately 10 seconds and then allowed to air dry for approximately 10 minutes. The site is then either extracted and the extracts analyzed, or analyzed directly using any techniques such as those exemplified above.

EXAMPLES

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention. Ingredients are identified by chemical or CTFA name, and all weights are in percent actives.

Examples 1–5

PHASE 1: SURFACTANT PHASE

In a suitable vessel, the following ingredients are mixed at room temperature. Once the polyquaternium is dispersed, the mixture is heated to 65° C.

| Ingredients | Weight Percent | | | | |
| --- | --- | --- | --- | --- | --- |
| | Example 1 | Example 2 | Example 3 | Example 4 | Example 5 |
| Water | QS 100 | QS 100 | QS 100 | QS 100 | QS 100 |
| Polyquaternium-10 | 0.25 | 0.25 | 0.25 | 0.25 | 0.25 |

While the above mixture is being heated to 65° C. the following ingredients are added to the mixture.

| | | | | | |
| --- | --- | --- | --- | --- | --- |
| Disodium EDTA | 0.10 | 0.10 | 0.10 | 0.10 | — |
| Ammonium Laureth Sulfate | 4.2 | 4.2 | 4.2 | 4.2 | — |
| Ammonium Lauryl Sulfate | 1.4 | 1.4 | 1.4 | 1.4 | — |
| Sodium Lauroamphoacetate | 2.4 | 2.4 | 2.4 | 2.4 | — |
| Sodium Lauroyl Sarcosinate | — | — | — | — | 4.0 |
| Disodium Lauroamphodiacetate & Sodium Trideceth Sulfate | — | — | — | — | 4.0 |

Once the above ingredients are thoroughly mixed begin cooling the mixture to 45° C. In a separate mixing vessel add the following:

| | | | | | |
| --- | --- | --- | --- | --- | --- |
| Water | 2.0 | 2.0 | 2.0 | 2.0 | 2.0 |
| Butylene Glycol | 2.0 | 2.0 | 2.0 | 2.0 | 2.0 |
| Glydant Plus | 0.2 | 0.2 | 0.2 | 0.2 | 2.0 |

Once the Glydant Plus is dissolved add this mixture to the first mixing vessel and cool to room temperature. Once cooled, apply 1.5 g of this solution to a non-woven substrate and then dry.

PHASE 2: CONDITIONING EMULSION:

In a suitable vessel, the following ingredients are mixed at room temperature and heated to 70° C. during mixing.

| | | | | | |
| --- | --- | --- | --- | --- | --- |
| SEFA* Cottonate | 4.65 | 4.00 | 4.65 | 34.40 | 4.65 |
| SEFA* Behenate | 0.35 | — | 0.35 | 2.60 | 0.35 |
| Petrolatum | — | 1.00 | — | — | — |
| Sorbitan Monooleate | — | — | — | 3.00 | — |
| Polyglycerl-4 Isostearate (and) Cetyl Dimethicone (and) Hexyl Laurate[1] | 5.00 | 5.00 | 5.00 | — | 5.00 |

[1]Available as Abil WE-09 from Goldschmidt
*SEFA is an acronym for sucrose esters of fatty acids Once the mixture reaches 70° C., stop heating and slowly add the following ingredients while continuing to mix:

| | | | | | |
| --- | --- | --- | --- | --- | --- |
| Glycerin | 90.00 | 90.00 | 70.00 | 60.00 | 90.00 |
| Panthenol | — | — | 20.00 | — | — |

Cool to Room Temperature while mixing. Then add 0.17 g of this phase to the substrate already containing the surfactants from the Surfactant Phase. The resulting cleansing composition is used by wetting with water and is useful for cleansing the skin or hair and for depositing the conditioning emulsions onto the skin or hair.

In alternative manufacturing procedures, the lathering surfactants, conditioning emulsions, and optional ingredients are separately or simultaneously added onto or impregnated into the water insoluble substrate by spraying, printing, splashing, dipping, or coating.

In alternative embodiments, other substrates such as woven substrates, hydroentangled substrates, natural sponges, synthetic sponges, or polymeric netted meshes are substituted for the present substrate.

Examples 6–10

PHASE 1: SURFACTANT PHASE

In a suitable vessel, the following ingredients are mixed at room temperature. Once the polyquaternium is dispersed, the mixture is heated to 65° C.

| Ingredients | Weight Percent | | | | |
| --- | --- | --- | --- | --- | --- |
| | Example 6 | Example 7 | Example 8 | Example 9 | Example 10 |
| Water | QS 100 | QS 100 | QS 100 | QS 100 | QS 100 |
| Glycerin | 10.0 | 10.0 | 10.0 | 10.0 | 10.0 |
| Polyquaternium-10 | 0.25 | 0.25 | 0.25 | 0.25 | 0.25 |
| Panthenol | — | — | 2.0 | 2.0 | 2.0 |
| Urea | 2.00 | 2.00 | 2.00 | 2.00 | 2.00 |

While the above mixture is being heated to 65° C. the following ingredients are added to the mixture.

| Disodium EDTA | 0.10 | 0.10 | 0.10 | 0.10 | 0.10 |
| --- | --- | --- | --- | --- | --- |
| Ammonium Laureth Sulfate | 4.2 | 4.2 | — | — | — |
| Ammonium Lauryl Sulfate | 1.4 | 1.4 | — | — | — |
| Sodium Lauroamphoacetate | 2.4 | 2.4 | — | — | — |
| Sodium Caproyl Lactylate | | | — | 3.33 | — |
| Sodium Lauroyl Methyl Taurate | | | 3.33 | — | — |
| Sodium Myristoyl Sarcosinate | | | — | — | 1.0 |
| Sodium Lauroyl Sarcosinate | — | — | — | — | 1.0 |
| Decylpolyglucoside | | | 3.33 | 3.33 | 4.0 |
| Cocamidopropyl betaine | | | 3.33 | 3.33 | 4.0 |
| Butylene Glycol | — | — | 2.00 | 2.00 | 2.00 |
| Methyl Paraben | — | — | 0.25 | 0.25 | 0.25 |
| Propylparaben | — | — | 0.15 | 0.15 | 0.15 |
| Phenoxyethanol | | | 0.5 | — | 0.3 |
| Benzyl Alcohol | — | — | — | 0.5 | 0.3 |

Once the above ingredients are thoroughly mixed begin cooling the mixture to 45° C. In a separate mixing vessel add the following:

| Water | 2.0 | 2.0 | — | — | — |
| --- | --- | --- | --- | --- | --- |
| Butylene Glycol | 2.0 | 2.0 | — | — | — |
| Glydant Plus | 0.2 | 0.2 | — | — | — |

Once the Glydant Plus is dissolved add this mixture to the first mixing vessel and cool to room temperature. Once cooled, apply 1.5 g of this solution to a non-woven substrate and then dry.

PHASE 2: CONDITIONING EMULSION:

In a suitable vessel, the following ingredients are mixed at room temperature and heated to 70° C. during mixing.

| SEFA* Cottonate | 27.36 | 27.36 | 27.36 | 27.36 | 27.36 |
| --- | --- | --- | --- | --- | --- |
| SEFA* Behenate | 6.84 | 6.84 | 6.84 | 6.84 | 6.84 |
| Petrolatum | 5.7 | 5.7 | 5.7 | 5.7 | 13.1 |
| C10–C30 cholesterol/lanosterol esters | 13.1 | 13.1 | 13.1 | 13.1 | 5.7 |
| Tocopherol Acetate | 1.14 | 1.14 | 1.14 | 1.14 | 1.14 |
| Glyceryl Tribehenate | 2.85 | 2.85 | 2.85 | 2.85 | 2.85 |
| Decaglyceryl Dipalmitate | 0.9 | — | — | — | — |
| Triglyceryl Monostearate | 2.1 | — | — | 2.1 | — |
| Decaglyceryl Stearate | — | 0.9 | 0.9 | 0.9 | 0.9 |
| Polyglyceryl Tristearate | — | 2.1 | 2.1 | — | 2.1 |

Once the mixture reaches 70° C., stop heating and slowly add the following ingredients while continuing to mix:

| Glycerin | 40.00 | 40.00 | 40.0 | 40.00 | 40.00 |
| --- | --- | --- | --- | --- | --- |

Cool to Room Temperature while mixing. Then add 0.20 g of this phase to the substrate already containing the surfactants from the Surfactant Phase. The resulting cleansing composition is used by wetting with water and is useful for cleansing the skin or hair and for depositing the conditioning emulsions onto the skin or hair.

In alternative manufacturing procedures, the lathering surfactants, conditioning emulsions, and optional ingredients are separately or simultaneously added onto or impregnated into the water insoluble substrate by spraying, printing, splashing, dipping, or coating.

In alternative embodiments, other substrates such as woven substrates, hydroentangled substrates, natural sponges, synthetic sponges, or polymeric netted meshes are substituted for the present substrate.

What is claimed is:

1. A disposable, single use personal care cleansing and conditioning product which, upon wetting, can be used to simultaneously cleanse and deposit conditioning agents onto the skin or hair, which product comprises:

(A) a water insoluble substrate, (B) a lathering surfactant added onto or impregnated into said substrate, and (C) a conditioning emulsion added onto or impregnated into said substrate separately from said lathering surfactant, wherein said product is substantially dry prior to use.

2. A product according to claim 1 wherein said lathering surfactant comprises from about 0.5% to about 40% by weight of said water insoluble substrate, and wherein said conditioning emulsion comprises from about 0.25% to about 150% by weight of said water insoluble substrate.

3. A product according to claim 1 wherein said conditioning emulsion comprises, (A) an internal phase comprising a water soluble conditioning agent selected from one or more water soluble agents such that the weighted arithmetic mean solubility parameter of said water soluble conditioning agent is greater than 10.5, and (B) an external phase comprising an oil soluble agent selected from one or more oil soluble agents such that the weighted arithmetic mean solubility parameter of said oil soluble conditioning agent is greater than 10.5.

4. A product according to claim 3 further comprising from about 0% to about 20% by weight of said conditioning emulsion of an emulsifier capable of forming an emulsion of said internal and external phases, wherein said emulsifier is selected from one or more emulsifiers such that the weighted arithmetic mean HLB value is from about 1 to about 10.

5. A product according to claim 3 wherein said oil soluble agent is selected from the group consisting of oil soluble conditioning agents, oil soluble non-conditioning agents, and mixtures thereof.

6. A product according to claim 5 wherein said oil soluble conditioning agent is selected from the group consisting of esters of fatty acids, fatty alcohols, ethoxylated alcohols, polyol polyesters, glycerin mono-esters, glycerin polyesters, epidermal and sebaceous hydrocarbons, lanolin, straight and branched hydrocarbons, silicone oil, silicone gum, vegetable oil, vegetable oil adduct, hydrogenated vegetable oils, non-ionic polymers, natural waxes, synthetic waxes, polyolefinic glycols, polyolefinic monoester, polyolefinic polyesters, cholesterols, cholesterol esters and mixtures thereof, and wherein said water soluble conditioning agent is selected from the group consisting of glycerin, glycerol, propylene glycol, polypropylene glycols, polyethylene glycols, ethyl hexanediol, hexylene glycols, other aliphatic alcohols, panthenol, urea, cationic polymers, polyols, glycolic acid, lactic acid, niacinamide, sodium PCA, sorbitol, and mixtures thereof.

7. A product according to claim 4 wherein said emulsifier is selected from the group consisting of sorbitan esters of C16–C22 saturated, unsaturated and branched chain fatty acids, glyceryl monoesters of C16–C22 saturated, unsaturated and branched chain fatty acids, polyglyceryl esters of C16–C22 saturated, unsaturated and branched chain fatty acids, methyl glucose esters of C16–C22 saturated, unsaturated and branched chain fatty acids, sucrose esters of C12–C22 saturated, unsaturated and branched chain fatty acids, C12–C22 ethoxylated fatty alcohols, hydrogenated castor oil ethoxylates, sorbitan ester ethoxylates, polymeric emulsifiers, silicone emulsifiers, and mixtures thereof.

8. A product according to claim 7 wherein said emulsifier is selected from the group consisting of sorbitan laurate, sorbitan palmitate, sorbitan monooleate, sorbitan isostearate, sorbitan sesquioleate, sorbitan monoisostearate, sorbitan stearates, sorbitan triooleate, sorbitan tristearate, sorbitan dipalmitate, glyceryl oleate, glyceryl monstearate, glyceryl monopalmitate, glyceryl monobehenate, polyglyceryl-4 isostearate, polyglyceryl-4 stearate, polyglyceryl-4 tristearate, polyglyceryl-4 pentastearate, polyglyceryl-2 isostearate, polyglyceryl-3 oleate, diglycerol monooleate, diglyceryl monostearate, triglyceryl monostearate, tetraglycerol monooleate, decaglyceryl dipalmitate, decaglyceryl monostearate, decaglyceryl stearate, decaglyceryl distearate, decaglyceryl pentastearate, decaglyceryl decastearate, sucrose stearate, sucrose trilaurate, sucrose distearate, methyl glucose dioleate, methyl glucose sesquiisostearate, oleth-2, oleth-3, steareth-2, PEG-7 hydrogenated castor oil, PEG-40 sorbitan peroleate, Polysorbate-80, ethoxylated dodecyl glycol copolymer, laurylmethicone copolyol, cetyldimethicone, dimethicone copolyol, and mixtures thereof.

9. A product according to claim 1 wherein said water insoluble substrate comprises one or more materials selected from the group consisting of silks, keratins, celluloses, acetates, acrylics, cellulose esters, modacrylics, polyamides, polyesters, polyolefins, polyvinyl alcohols, and mixtures thereof.

10. A product according to claim 9 wherein said water insoluble substrate comprises one or more materials selected from the group consisting of wood pulp, cotton, hemp, jute, flax, acrylics, nylons, polyesters, polypropylenes, polyethylenes, polyvinyl acetates, polyurethanes, rayon, and mixtures thereof.

11. A product according to claim 10 wherein said water insoluble substrate is selected from the group consisting of nonwoven substrates, woven substrates, hydroentangled substrates, atural sponges, synthetic sponges, polymeric netted meshes, formed films, and mixtures thereof.

12. A product according to claim 11 wherein said water insoluble substrate comprises a nonwoven sheet of fibers selected from the group consisting of rayon fibers, cellulose fibers, polyester fibers, and mixtures thereof.

13. A product according to claim 1 wherein said lathering surfactant is selected from the group consisting of anionic lathering surfactants, nonionic lathering surfactants, amphoteric lathering surfactants, and mixtures thereof.

14. A product according to claim 13 wherein said anionic lathering surfactant is selected form the group consisting of sarcosinates, sulfates, isethionates, phosphates, taurates, lactylates, glutamates and mixtures thereof; wherein said nonionic lathering surfactant is selected from the group consisting of amine oxides, alkyl glucosides, alkyl polyglucosides, polyhydroxy fatty acid amides, alkoxylated fatty acid esters, sucrose esters, and mixtures thereof; and wherein said amphoteric lathering surfactant is selected from the group consisting of betaines, sultaines, hydroxysultaines, alkyliminoacetates, iminodialkanoates, aminoalkanoates, and mixtures thereof.

15. A product according to claim 14 wherein said anionic lathering surfactant is selected from the group consisting of ammonium lauroyl sarcosinate, sodium trideceth sulfate, sodium lauroyl sarcosinate, sodium myristoyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium lauroyl lactylate, triethanolamine lauroyl lactylate, sodium caproyl lactylate, sodium lauroyl methyl taurate, sodium cocoyl methyl taurate, sodium lauroyl glutamate, sodium myristoyl glutamate, and sodium cocoyl glutamate and mixtures thereof; wherein said nonionic lathering surfactant is selected from the group consisting of lauramine oxide, cocoamine oxide, decyl polyglucose, lauryl polyglucose, C12–14 glucose amides, sucrose cocoate, sucrose laurate, and mixtures thereof; and wherein said amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

16. A product according to claim 1 wherein said cleansing product further comprises a safe and effective amount of one or more active ingredients selected from the group consisting of anti-acne actives, vitamins, anti-wrinkle and anti-skin actives, non-stearoidal anti-inflammatory actives, topical anesthetics, artificial tanning agents and accelerators, anti-microbial and anti-fungal agents, sunscreen actives, anti-oxidants, and mixtures thereof.

17. A product according to claim 16 wherein said active ingredient is selected from the group consisting of salicylic acid, benzoyl peroxide, cis-retinoic acid, trans-retinoic acid, retinol, retinyl palmitate, phytic acid, N-acetyl L-cysteine, azelaic acid, lipoic acid, resorcinol, ascorbic acid and derivatives thereof, ibuprofen, naproxen, hydrocortisone, phenoxyethanol, phenoxypropanol, phenoxyisopropanol, 2,4,4,'-trichloro-2'-hydroxy diphenyl ether, 3,4,4'-trichlorocarbanilide, 2-ethylhexyl p-methoxycinnamate, oxybenzone, 2-phenylbenzimidozole-5-sulfonic acid, dihydroxyacetone, and mixtures thereof.

18. A product according to claim 1 further comprising a compound selected from the group consisting of water soluble conditioning agent, oil soluble agent, active ingredients, and mixtures thereof, wherein said compound is separately or simultaneously added onto or impregnated into said water insoluble substrate in addition to the conditioning emulsion.

19. A disposable, single use personal care cleansing and conditioning product which, upon wetting, can be used to simultaneously cleanse and deposit conditioning agents onto the skin or hair, which product comprises (A) a water insoluble substrate,
(B) a lathering surfactant, and
(C) a conditioning emulsion comprising,
  (i) an internal phase comprising a water soluble conditioning agent, and
  (ii) an external phase comprising an oil soluble agent, wherein said lathering surfactant and said conditioning emulsion are separately added onto or impregnated into said water insoluble substrate, and wherein said product is substantially dry prior to use.

20. A method of manufacturing a disposable, single use personal care cleansing and conditioning product which, upon wetting, can be used to simultaneously cleanse and deposit conditioning agents onto the skin or hair, which method comprises the step of separately adding onto or impregnating into a water insoluble substrate
   (A) a lathering surfactant, and
   (B) a conditioning emulsion comprising,
      (i) an internal phase comprising a water soluble conditioning agent, and
      (ii) an external phase comprising an oil soluble agent,
wherein said resulting product is substantially dry prior to use.

21. A method of manufacturing a product according to claim 20 wherein the lathering surfactant and said conditioning emulsion are separately or simultaneously added onto or impregnated into the water insoluble substrate by spraying, printing, splashing, dipping, or coating.

22. A method of depositing water soluble conditioning agents to the surface of the skin or hair using the product of claim 1.

23. A method of cleansing and conditioning the skin or hair with a personal cleansing product, which method comprises the steps of:
   (A) wetting with water a substantially dry, disposable, single use personal cleansing product comprising:
      (i) a water insoluble substrate,
      (ii) a lathering surfactant, added onto or impregnated into said substrate, and
      (iii) a conditioning emulsion added onto or impregnated into said substrate separately from said lathering surfactant, which conditioning emulsion comprises:
         (a) an internal phase comprising a water soluble conditioning agent, and
         (b) an external phase comprising an oil soluble agent,
   (B) contacting the skin or hair with said wetted product, and
   (C) rinsing the skin or hair.

* * * * *

UNITED STATES PATENT AND TRADEMARK OFFICE
CERTIFICATE OF CORRECTION

PATENT NO.    : 5,951,991
DATED         : September 14, 1999
INVENTOR(S)   : Julie Ann Wagner et al.

It is certified that error appears in the above-identified patent and that said Letters Patent is hereby corrected as shown below:

At column 7, line 17 "conforming" should read --coforming--.

At column 14, line 62 "$\sum_i \sum_i$" should read --$\sum_i E_i$--.

At column 18, line 59 "monoethanolanine" should read --monoethanolamine--.

At column 20, line 31 "thereof, polyglyceryl" should read --thereof; polyglyceryl--.

At column 29, line 65 insert --* SEFA is an acronym for sucrose esters of fatty acids--.

At column 31, line 56 "atural" should read --natural--.

At column 32, line 61 "comprises" should read --comprises:--.

Signed and Sealed this

Twenty-second Day of August, 2000

Attest:

Q. TODD DICKINSON

*Attesting Officer*          *Director of Patents and Trademarks*